United States Patent [19]

Umezawa et al.

[11] 3,953,594
[45] Apr. 27, 1976

[54] PROCESS FOR PREPARING BLEOMYCIN GROUP ANTIBIOTICS

[75] Inventors: Hamao Umezawa, Tokyo; Tomohisa Takita, Asaka; Yasuhiko Muraoka, Tokyo; Akio Fujii, Yono, all of Japan

[73] Assignee: Zaidan Hojin Biseibutsu Kagaku Kenkyu Kai, Tokyo, Japan

[22] Filed: Aug. 7, 1973

[21] Appl. No.: 386,329

Related U.S. Application Data

[63] Continuation-in-part of Ser. No. 280,043, Aug. 11, 1972, abandoned.

[30] Foreign Application Priority Data

Aug. 13, 1971 Japan.............................. 46-61063

[52] U.S. Cl. .............................. 424/117
[51] Int. Cl.² ........................... H61K 35/00
[58] Field of Search ...................... 424/117

[56] References Cited
OTHER PUBLICATIONS
Ikekawa et al., J. of Antibiotics, XVII-5, XVII-5, 1964, pp. 194–199.

Primary Examiner—Jerome D. Goldberg
Attorney, Agent, or Firm—Oblon, Fisher, Spivak, McClelland & Maier

[57] ABSTRACT

This invention is concerned with the oxidative conversion of an unstable phleomycin group to a stable bleomycin group antibiotic having the partial structure:

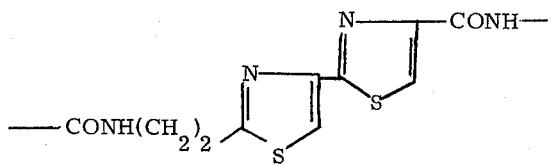

by treatment with potassium ferricyanide or manganese dioxide.

1 Claim, 2 Drawing Figures

PROCESS FOR PREPARING BLEOMYCIN GROUP ANTIBIOTICS

RELATIONSHIP TO PREVIOUS APPLICATIONS

This is a continuation-in-part application of copending application Ser. No. 280,043, filed Aug. 11, 1972, now abandoned.

BACKGROUND OF THE INVENTION

1. Field of the Invention:

This invention relates to a process for preparing stable bleomycin group antibiotics from unstable phlomycin group antibiotics susceptible to oxidation.

2. Description of the Prior Art:

Phleomycin, which is a glycopeptide antibiotic, was isolated in 1956, as disclosed in *The Journal of Antibiotics*, A9, 82–25 (1956); A12, 111 (1959): A12, 285–289 (1959). Isolation of phleomycin in high yield is difficult, however, because of its inherent instability under acidic conditions. Various antibiotics such as bleomycin similar to phleomycin, which are stable under acidic conditions, have been studied as disclosed in *The Journal of Antibiotics*, A19, 200–209 (1966). Structural elucidation studies of bleomycin group antibiotics have revealed that it possesses the following partial structure:

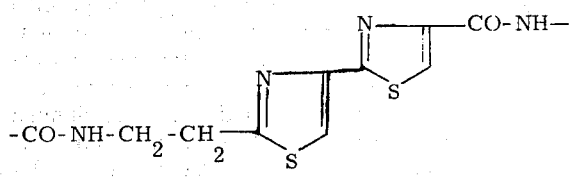

(II)

Furthermore, structural studies of phleomycin group antibiotics have shown that it has the partial structure:

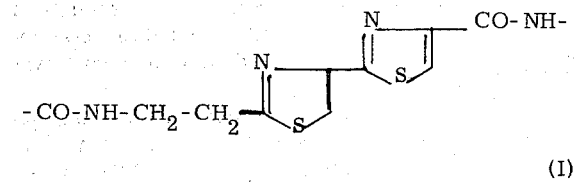

(I)

These studies have also revealed that the partial structure (I) is unstable and can be readily converted to partial structure (II) to form a stable biologically active bleomycin group antibiotics.

SUMMARY OF THE INVENTION

Accordingly, it is an object of this invention to provide a process for preparing stable bleomycin group antibiotics from unstable phleomycin group antibiotics.

Briefly, this object and other objects of this invention are achieved by providing a process for preparing stable bleomycin group antibiotics having the partial structure:

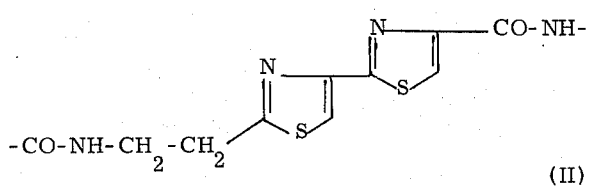

(II)

in the molecule by oxidation of unstable phleomycin group antibiotics having the partial structure:

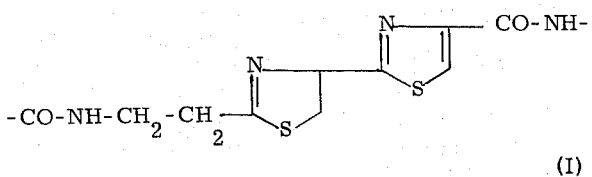

(I)

BRIEF DESCRIPTION OF THE DRAWINGS

Various other objects, features and attendant advantages of the invention will become better understood by reference to the attached Drawings, wherein:

FIG. I is a plot of ultraviolet absorption at 280 m$\mu$ versus different eluent fractions containing phleomycin compounds; and, FIG. II is a plot of ultraviolet absorption at 280 m$\mu$ versus different eluent fractions containing phleomycin compounds which were exposed to an oxidizing agent.

DESCRIPTION OF THE PREFERRED EMBODIMENTS

Figure 1:
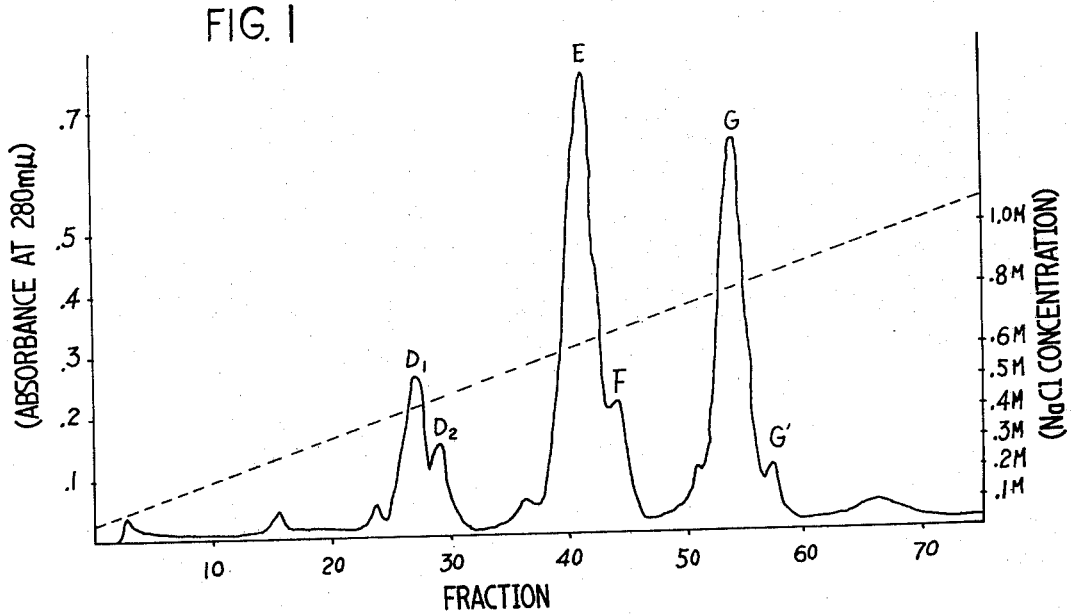

Since the isolation of various phleomycin and bleomycin antibiotics, further studies on other antibiotics produced by Streptomyces have been conducted. Other phleomycin group antibiotics produced by Streptomyces flavoviridis were isolated whose molecular structure contain the unstable partial structure illustrated in structure (I) which can be phleomycin $D_1$, E, or G, a crude mixture thereof, 3-S, S-dimethylmercaptopropylamino-phleomycin, 3-morpholinopropylamino-phleomycin, 3-N,N-dimethylaminopropylamino-phleomycin or YA-56. These compounds may be converted to stable biologically active bleomycin group antibiotics in accordance with the process of this invention. The antibiotic YA-56, which is disclosed in *The Journal of Antibiotics*, 24, No. 10, 727–731, is one of the unstable phleomycin group antibiotics which are glycopeptides having the partial structure (I) in the molecular. Antibiotic YA-56 was isolated from the culture broth of a Streptomyces humidus variant, and was produced by fermentation of the strain for 5–7 days at 27°C. in a liquid medium containing glucose, glycerol, dextrine, soybean meal, NaCl, $CaCO_3$ and $CuSO_4$. These unstable phleomycin group antibiotics having the partial structure (I) in the molecule can be used as the starting materials of this invention. The phleomycin group antibiotics can be separated from the fermentation cultures by extraction in a form which contains copper in the molecule. Suitable antibiotics useful as starting materials for the processes of this invention may contain copper in the molecules, or may have the copper removed by treatment with hydrogen sulfide.

The process of this invention can be applied to convert all of the unstable phleomycin group antibiotics having the partial structure (I) to stable bleomycin group antibiotics having the partial structure (II). In the process of this invention, various oxidizing agents convert the thiazoine ring in the partial structure (I) to the thiazole ring in the partial structure (II). Suitable oxidizing agents are potassium ferricyanide and manganese dioxide. Conventional oxidation processes using these oxidizing agents are suitable processes for this invention.

The phleomycin group antibiotics with the partial structures (I) and bleomycin group antibiotics with the partial structure (II) have characteristics ultraviolet absorption spectra. The phleomycin group antibiotics with the partial structure (I) have an ultraviolet absorption spectrum with absorption maxima of $E_{1cm}^{1\%}$ 140 – 160 at about 244m$\mu$ and $E_{1cm}^{1\%}$ 50–60 at about 300 m$\mu$. The bleomycin group antibiotics with the partial structure (II) have an ultraviolet absorption spectrum with absorption maxima of $E_{1cm}^{1\%}$ 150–170 at about 244 m$\mu$ and $E_{1cm}^{1\%}$ 120–135 at about 293 m$\mu$. The absorption maxima for both partial structures occur at approximately the same wavelengths. However, structural identification of each partial structure from its UV spectra is still possible because the ratio of the longer wavelength absorption maximum to the shorter wavelength absorption maximum is about 2.8 for antibiotics having the partial structure (I) and about 1.2 for antibiotics having the partial structure (II).

In the preparation of the bleomycin group antibiotics having the partial structure (II) by oxidation of the phleomycin group antibiotics having the partial structure (I), the latter antibiotic is dissolved in a solvent such as water, methanol, etc., and 1 mole to 50 moles of a mild oxidizing agent per 1 mole of phleomycin group antibiotics is added to the solution. When manganese dioxide is used as the oxidizing agent, it is dispersed in a solvent and reacted at 0°–50°C. for 20–240 hours in the pH 6.5 to 9. The reaction mixture contains both the oxidized product having the partial structure (II) and the starting material having the partial structures (I). In order to separate them, the reaction mixture is dissolved in water and is passed through a column packed with an exchange resin (CM-Sephadex C-25) pretreated with a sodium chloride solution. After absorption of the materials, the materials are eluted with a sodium chloride eluent whereby the unreacted starting material is eluted first and then the oxidized antibiotic is eluted. The solution containing the oxidized antibiotic is absorbed by a conventional method in which the antibiotic is washed with water to remove the inorganic salts, and then treated with a dilute HCl-acetone mixture to elute the oxidized product. The solution is adjusted to pH 6.0 by the addition of a base exchanged anion resin, and the hydrochloride of the oxidized antibiotic is obtained by removal of the solvent through distillation. The unstable phleomycin group antibiotics having the partial structure (I) are difficult to purify by extraction.

The process of this invention can be conducted very advantageously in industrial operations by treating the crude material containing impurities from the fermentation tanks before the extraction purification process with a cation exchange resin. The crude product is converted to a mixture of stable bleomycin group antibiotics having the partial structure (II), and then purified to isolate the oxidized product. For example, phleomycin compounds are produced by the conventional tank fermentation method, and, after filtration, the filtrate is absorbed on a cation exchange resin (Ambarite IRC-50 H type) and eluted with dilute HCl. The obtained solution is neutralized and, the material eluted from the resin, is absorbed on active carbon and washed with water to remove the inorganic salts. The material is eluted from the carbon absorbent with a dilute HCl-acetone mixture, and the solution is adjusted to pH 6.0 by the addition of an anion exchange resin. After the acetone is distilled from the solution to yield an aqueous solution containing crude phleomycin compounds. These compounds are then oxidized by the process of this invention to convert the unstable phleomycin group antibiotics having the partial structure (I) to the stable bleomycin group having the partial structure (II). The oxidized product is then separated and purified. The process of this invention provides the advantages of a remarkably increased yield of purified product and a better separation of the stable antibiotics. Phleomycins were produced by the conventional tank fermentation method and were purified by chromatographic separation using active carbon, alumina and Sephadex. The purified phleomycin mixture was further separated by chromatography using CM-Sephadex C-25. The results of the separation and purification procedures are shown in FIG. 1, wherein the absorbance at 280 m$\mu$ is shown versus the number of eluent fractions. The dotted line represents the concentration of sodium chloride in the eluent fractions, and the letters at the peaks of each elution curve represent different phleomycin components. Analysis of ultraviolet absorption spectra confirmed that the phleomycins, $D_1$, E and G shown in FIG. 1 have the partial structure (I), and the components $D_2$, F and G' have the partial structure (II). The information obtained from the physiochemical properties and acid hydrolysis products of component $D_2$ and component F revealed that component $D_2$ was bleomycin $B_2$ and that component F was bleomycin $B_4$.

Figure 2:
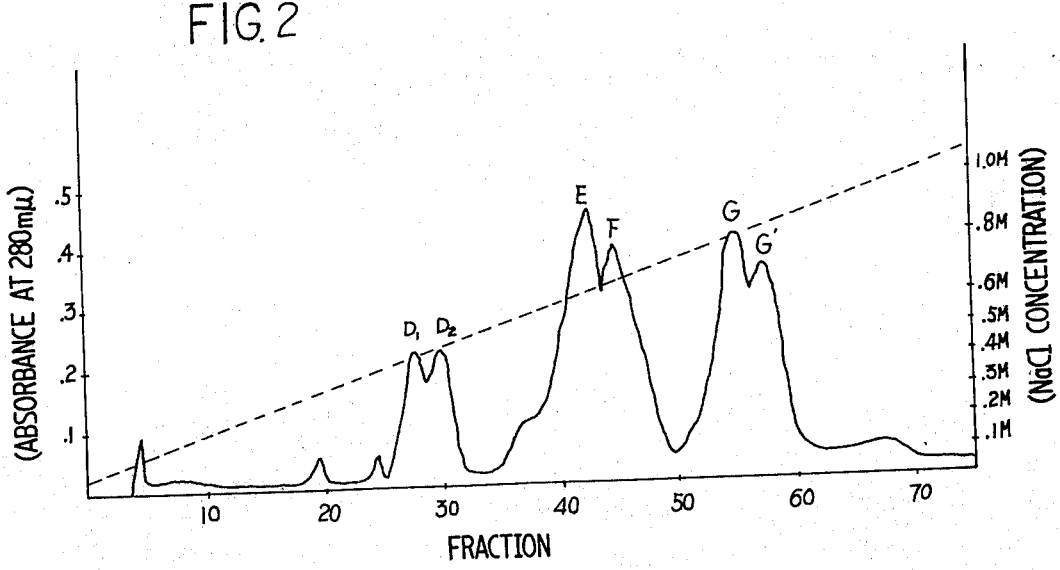

The phleomycin mixture was oxidized with manganese dioxide, and separation of the products was accomplished by chromatography using CM-Sephadex under the same conditions revealed earlier. The results are shown in FIG. II, wherein the peaks corresponding to the phleomycin components $D_1$, E and G decreased and the peaks corresponding to the phleomycin components $D_2$, F and G' increased. According to comparative test results from the acid hydrolysis products of the components, it is determined that the following conversions occured as shown in FIG. 2:

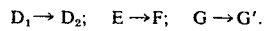

A 500 mg. sample of the crude phleomycin mixture and the same quantity of the crude mixture oxidized with manganese dioxide were both separated by use of CM-Sephadex chromatography. The amounts of each component in the unoxidized phleomycin mixture and the oxidized mixture are shown in the following Table:

| Ingredient | Unoxidized phleomycin | Oxidized Product |
|---|---|---|
| $D_1$ | 39 mg. | 17 mg. |
| $D_2$ | 22 mg. | 40 mg. |
| E | 114 mg. | 56 mg. |
| F | 33 mg. | 69 mg. |
| G | 96 mg. | 43 mg. |
| G' | 17 mg. | 45 mg. |

Having now generally described the invention, a further understanding can be obtained by reference to certain specific Examples which are provided herein for purposes of illustration only and are not intended to be limiting in any manner unless otherwise specified.

EXAMPLE 1

Phleomycin $D_1$ (Cu-containing hydrochloride) which has a absorption maximum of $E_{1cm}^{1\%}$ 147 at 244 m$\mu$ and an absorption maximum of $E_{1cm}^{1\%}$ 54 at 300 m$\mu$ plus additional minor ultraviolet absorption in its spectrum in methanol, was used in the following procedure. A 20 mg. quantity of powdery phleomycin $D_1$ was dissolved in 1 milliliter of water and 20 mg. of manganese dioxide was suspended in the solution. The mixture was reacted at room temperature for 40 hours with stirring. After the reaction, the solution was filtered and the filtrate was passed through a column packed with CM-Sephadex C-25 pretreated with a 0.05 M sodium chloride solution to absorb the reaction products. After absorption of the products, the concentration of the sodium chloride solution as the eluent was linearly increased from 0.05 M to 1 M. As a result of this procedure, unreacted phleomycin $D_1$ was eluted in the fraction containing 0.40 M sodium chloride, and a bleomycin derivative was eluted in the fraction containing 0.44 M sodium chloride. The latter fraction was passed through a column packed with 1 milliliter of active carbon to absorb the bleomycin derivative. The column was washed with water to remove inorganic salts and then an eluent of a 1 : 1 acetone - 0.02N HCl solution was passed through the column to elute a blue solution containing the bleomycin derivative (Cu-containing hydrochloride). An anion exchange resin (Dow X-44, OH type) was added to the blue solution to adjust the solution to pH 6.0. The blue solution was filtered, the solvent was removed and the product dried to yield 12 mg. of a blue powdery bleomycin derivative (Cu-containing hydrochloride).

The bleomycin derivatives had the specific ultraviolet absorption spectrum in methanol characteristic of glycopeptides having the partial structure (II) with an absorption maximum of $E_{1cm}^{1\%}$ 159 at 244 m$\mu$, an absorption maximum of $E_{1cm}^{1\%}$ 127 at 293 m$\mu$, and other minor absorption patterns.

The bleomycin derivative had an Rf value of 0.66, on a silica gel thin layer chromatogram using the following eluent composition, $CH_3OH$ : 10%—$CH_3COONH_4$ : 10%—$NH_4OH$ = 10 : 9 : 1 and an Rf value of 0.56 on an Avicel thin layer chromatogram using the following eluent composition, $CH_3CH_2CH_2OH$ : pyridine : $CH_3COOH$: $H_2O$ = 15 : 10 : 3 : 12.

The bleomycin derivative was confirmed to be bleomycin $B_2$ because the chromatographic data obtained was the same as that from an authentic sample of bleomycin $B_2$. The hydrolysis decomposition products of the bleomycin derivative are shown in Table 1 and were the same products obtained upon hydrolysis of an authentic sample of bleomycin $B_2$.

TABLE I

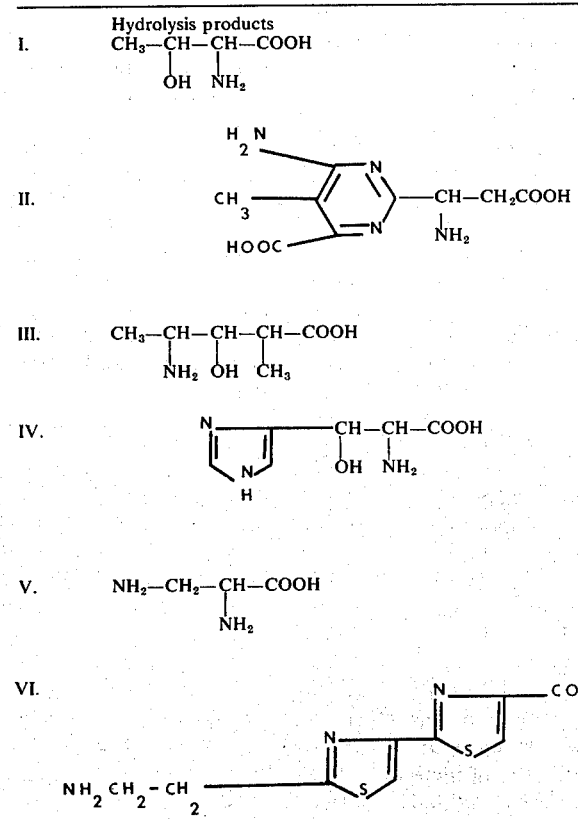

Hydrolysis products

I. $CH_3-CH-CH-COOH$ with OH, $NH_2$ substituents

II. Pyrimidine structure with $H_2N$, $CH_3$, $HOOC$ substituents and $-CH-CH_2COOH$ with $NH_2$ III. $CH_3-CH-CH-CH-COOH$ with $NH_2$, OH, $CH_3$ substituents IV. Imidazole ring with $-CH-CH-COOH$ and OH, $NH_2$ substituents V. $NH_2-CH_2-CH-COOH$ with $NH_2$ VI. $NH_2CH_2-CH_2-$ linked to bithiazole with COOH

TABLE I-continued

VII. 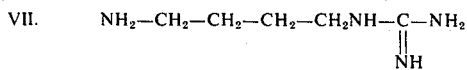

Antimicrobial activity to Mycobacterium 607 of the bleomycin derivative by the cup assay method was 2720 U/mg. (The free base of standard bleomycin A gave a value of 1,000 U/mg.

The stability of the bleomycin derivative and the starting material of phleomycin $D_1$ were compared in acidic solution conditions. A 1.0 mg. sample of the bleomycin derivative and a 1.0 mg. sample of phleomycin $D_1$ were dissolved in 10 milliliters of a 0.01-HCl solution and the solutions were maintained at pH 2 at 27°C. for 1 hour. The residual antimicrobial activity of both materials to Mycobacterium 607 by the cup assay method was measured and is shown in Table II as the ratio of 100 to the initial antimicrobial activity.

TABLE II

| Time (hr.) | 0 | 1 | 6 | 4 | 72 |
|---|---|---|---|---|---|
| bleomycin derivative | 100 | 102 | 97 | 99 | 102 |
| phleomycin $D_1$ | 100 | 20.8 | 5.3 | 2.7 | 0 |

EXAMPLE 2

A 20 mg. sample of powdery phleomycin E (Cu-containing hydrochloride) in methanol had an absorption maximum of $E_{1cm}^{1\%}$ 154 at 244 m$\mu$, an absorption maximum of $E_{1cm}^{1\%}$ 57 at 300 m$\mu$, and other minor absorption patterns in its ultraviolet absorption spectrum. The material was oxidized and the resulting product was separated by chromatography using CM-Sephadex C-25 in accordance with the process of Example 1. In the separation and purification process, the unreacted phleomycin E was eluted in the fraction containing 0.60 M sodium chloride, and a bleomycin derivative was eluted in the fraction containing 0.64 M sodium chloride. In accordance with the process of Example 1, the latter fraction was absorbed on active carbon, the associated inorganic salts were removed, the solution was neutralized and the solvent was removed to yield a dried product consisting of 10 mg. of a blue powdery bleomycin derivative (Cu-containing hydrochloride).

The bleomycin derivative in methanol had the specific ultraviolet absorption spectrum characteristic of glycopeptides having the partial structure (II), and had an absorption maximum of $E_{1cm}^{1\%}$ 162 at 244 m$\mu$, an absorption maximum of $E_{1cm}^{1\%}$ 130 at 293 m$\mu$, and other minor absorption patterns.

Confirmation of the bleomycin derivative as bleomycin $B_4$ was obtained by its Rf value of 0.50 upon silica gel thin layer chromatography using an eluent of $CH_3OH$ : 10% —$CH_3COONH_4$ : 10% — $NH_4OH$ = 10 : 9 : 1 and by its Rf value of 0.54 upon A vicel thin layer chromatography using an eluent of $CH_3CH_2CH_2OH$ : pyridine : $CH_3COOH$ : $H_2O$ = 15 : 10 : 3 : 12.

Antimicrobial activity to Mycobacterium 607 of the bleomycin derivative by the cup assay method was 6354 U/mg (the free base of standard bleomycin $A_2$ gave a value of 1,000 U/mg). The stability of the bleomycin derivative (confirmed as bleomycin $B_4$) and the starting material of phleomycin $D_1$ in acidic solution conditions were compared as shown in Table III.

TABLE III

| Time (hr.) | 0 | 24 |
|---|---|---|
| the resulting bleomycin $B_4$ | 100 | 95 |
| phleomycin E | 100 | 1.8 |

EXAMPLE 3

A 20 mg. sample of powdery phleomycin $D_1$ (Cu-free hydrochloride) in methanol, had an absorption maximum of $E_{1cm}^{1\%}$ 150 at 244 m$\mu$, an absorption maximum of $E_{1cm}^{1\%}$ 56 at 300 m$\mu$, and other minor absorption patterns in its ultraviolet absorption spectrum. The material was oxidized and the resulting product was separated by chromatography using CM-Sephadex C-25 in accordance with the process of Example 1. In the separation and purification processes, the unreacted phleomycin $D_1$ was eluted in the fraction containing 0.42 M sodium chloride, and a bleomycin derivative was eluted in the fraction containing 0.46 M sodium chloride. In accordance with the process of Example 1, the latter fraction was absorbed on active carbon, the associated inorganic salts were removed, the solution was neutralized and the solvent was removed to yield a dried product consisting of 9 mg. of a colorless powdery bleomycin derivative (Cu-free hydrochloride).

The bleomycin derivative in methanol (containing $CuSO_4$) had the specific ultraviolet absorption spectrum characteristic of glycopeptides having the partial structure (II) and had an absorption maximum of $E_{1cm}^{1\%}$ 161 at 244 m$\mu$, an absorption maximum of $E_{1cm}^{1\%}$ 127 at 293 m$\mu$, and edge absorption. The bleomycin derivative was confirmed as bleomycin $B_2$ by its Rf value of 0.61 upon slica gel thin layer chromatography using an eluent of $CH_3OH$ : 10%—$NH_4OH$ = 10 : 9 : 1 and by its Rf value of 0.48 upon Avicel thin layer chromatography using an eluent of $CH_3CH_2CH_2OH$ : pyridine : $CH_3COOH$ : $H_2O$ = 15 : 10 : 3 : 12. Antimicrobial activity to Mycobacterium 607 of the bleomycin derivative by the cup assay method was 2680 U/mg. (the free base of standard bleomycin $A_2$ gave a value of 1,000 U/mg.

EXAMPLE 4

A 20 mg. sample of powdery phleomycin $D_1$ (Cu-containing hydrochloride) in methanol had an absorption maximum of $E_{1cm}^{1\%}$ 147 at 244 m$\mu$, an absorption maximum of $E_{1cm}^{1\%}$ 54 at 300 m$\mu$, and other minor absorption patterns in its ultraviolet absorption spectrum. This material and 20 mg. of potassium ferricyanide were dissolved in 1 milliliter of water and reacted at room temperature for 48 hours. After the reaction, the reaction mixture was passed through a column packed with 30 milliliters of CM-Sephadex C-25 pretreated with a 0.05 M sodium chloride solution. The potassium ferricyanide and some reaction products thereof passed through the column but phleomycin reaction products were absorbed to form a blue band at the upper part of the column. The concentration of the sodium chloride eluent was linearly increased from 0.50 M to 1.0 M in the elution of the reaction product. In the separation and purification process, the unreacted phleomycin $D_1$ was eluted in the fraction containing 0.40 M sodium chloride, and bleomycin derivative was eluted in the fraction containing 0.44 M sodium chloride.

In accordance with the process of Example 1, the latter fraction was absorbed on active carbon, the associated inorganic salts were removed, the solution was neutralized and the solvent was removed to yield a dried product consisting of 6 mg. of a blue powdery bleomycin derivative (Cu-containing hydrochloride).

The bleomycin derivative in methanol had the specific ultraviolet absorption spectrum characteristic of glycopeptides having the partial structure (II) and had an absorption maximum of $E_{1cm}^{1\%}$ 156 at 244 m$\mu$, an absorption maximum of $E_{1cm}^{1\%}$ 124 at 293 m$\mu$, and other minor absorption patterns. The bleomycin derivative was confirmed as bleomycin $B_2$ by its Rf value of 0.66 upon silica gel thin layer chromatography using an eluent of $CH_3OH : 10\%—CH_3COONH_4 : 10\% — NH_4OH = 10 : 9 : 1$ and by its Rf value of 0.56 upon Avicel thin layer chromatography using an eluent of $CH_3CH_2CH_2OH : $ pyridine $ : CH_3COOH: H_2O : e15 : 10 : 3 : 12$.

EXAMPLE 5

A 100 mg. sample of YA-56 (Cu-containing hydrochloride) consisting of 70 mg. of an X component in methanol having an absorption maximum of $E_{1cm}^{1\%}$ 126.6 at 246.5 m$\mu$, an absorption maximum of $E_{1cm}^{1\%}$ 45.6 at 300–303 m$\mu$, and other minor absorption patterns, and 30 mg. of a Y component in methanol having an absorption maximum of $E_{1cm}^{1\%}$ 134 at 245.5 m$\mu$, an absorption maximum of $E_{1cm}^{1\%}$ 47 at 302 m$\mu$, and other minor absorption patterns, was dissolved in distilled water and was adjusted to pH 7.5 by the addition of 1N-sodium bicarbonate. Twenty mg. of manganese dioxide powder was added to the solution, stirred at 5°–8°C. for 9 days and filtered to remove the manganese dioxide. The filtrate was concentrated under reduced pressure and was dried to yield 96 mg. of crude powder. The product was dissolved in 0.05N—HCl and was maintained at room temperature for 16 hours. The solution was adjusted to pH 6.0 by the addition of a sodium hydroxide solution, and the product was absorbed in a column packed with 100 milliliters of CM-Sephadex C-25 ($Na^+$ type). The concentration of the sodium chloride eluent solutions were linearly increased from 0.05 M to 1.0 M in which the total amount of sodium chloride solution used was 1 liter. The dehydro YA-56 Y component was eluted in the fraction containing 0.32 M sodium chloride, and the dehydro YA-56 X component was eluted in the fraction containing 0.38 M of sodium chloride. Unreacted YA-56 Y component was eluted in the fraction containing 0.44 M sodium chloride and the unreacted YA-56 X component was eluted in the fraction containing 0.48 M sodium chloride.

In accordance with the process of Example 1, the X and Y components were absorbed separately on active carbon, the associated inorganic salts were removed, the solutions were neutralized and the solvents were removed to yield dried products consisting separately of 32 mg. of violet-blue powdery dehydro YA-56 X component and 12 mg. of dehydro YA-56 Y component. The resulting dehydro YA-56 X component had an ultraviolet absorption spectrum in methanol having absorption maxima of $E_{1cm}^{1\%}$ 153 at 243 m$\mu$, and $E_{1cm}^{1\%}$ 116 at 293 m$\mu$.

The resulting dehydro YA-56 Y component had an ultraviolet absorption spectrum in methanol having absorption maxima of $E_{1cm}^{1\%}$ 152 at 242 m$\mu$, and $E_{1cm}^{1\%}$ 117 at 292 m$\mu$.

The structure of the X and Y components were confirmed as YA-56 X and YA-56 Y by their respective Rf values of 0.68 and 0.71 upon silica gel thin layer chromatography using an eluent of $CH_3OH : 10\%—CH_3CO_2NH_4 : 10\%—NH_4OH = 10 : 9 : 1$. Rf values of 0.56 and 0.66 were obtained respectively for the YA-56 X component and the YA-56 Y component upon Avicel thin layer chromatography using an eluent of $CH_3CH_2CH_2OH : $ pyridine $ : CH_3COOH: H_2O = 15 : 10 : 3 : 12$. Antimicrobial activity to Mycobacterium 607 of the YA-56 X component and the YA-56 Y component by the cup assay method were 2665 U/mg and 1848 U/mg, respectively (the free base of standard bleomycin $A_2$ gave a value of 1,000 U/mg).

Among the hydrolyzate products from the acid catalyzed hydrolysis of the dehydro YA-56 X and Y components, amino acid VI in Table 1 was found. A positive ninhydrin spot characteristic for YA-56 was achieved by the use of two-dimensional paper chromatography. The stability of the dehydro-YA-56 X and dehydro YA-56 Y compounds were measured in accordance with the procedure of Example 1, and the results are shown in Table IV.

TABLE IV

| Time (hr.) | 0 | 24 |
| --- | --- | --- |
| dehydro YA-56 X | 100 | 96 |
| Dehydro YA-56 Y | 100 | 94 |
| YA-56 X | 100 | 4.5 |
| YA-56 Y | 100 | 3.8 |

EXAMPLE 6

100 mg. (0.065 m mol) of powdery 3-S, S-dimethylmercaptopropylamino-phleomycin (Cu-containing hydrochloride) which has the absorption maximum of $E_{1cm}^{1\%}$ 158 at 244 m$\mu$, and the other absorption maximum of $E_{1cm}^{1\%}$ 55 at 300 m$\mu$, and end absorption of ultraviolet absorption spectrum in methano., (activity to Mycobacterium Smegmatis 607 of 865 u/mg) was dissolved in 5 ml of water and 50 mg 0.575 m mole of manganese dioxide was suspended in the solution and reacted at 5°C pH 6.5 for 58 hours with stirring. After the reaction, the solution was filtered. The filtrate was absorbed and eluted by using a chromatography. The unreacted phleomycin was eluted in the fraction of 0.28 M of sodium chloride elute and the object product of 3-S, S-dimethylmercaptopropylamino-bleomycin (bleomycin $A_2$ Cu-containing hydrochloride) was eluted in the fraction of 0.33 M of sodium chloride elute. The solution of the bleomycin $A_2$ eluted as the latter fraction was treated in accordance with Example 1 to obtain 40 mg of blue powdery bleomycin $A_2$ (Cu-containing hydrochloride).

The product has the absorption maximum of $E_{1cm}^{1\%}$ 161 at 244 m$\mu$ and the absorption maximum of $E_{1cm}^{1\%}$ 130 at 293 m$\mu$ and end absorption of ultraviolet absorption spectrum in methanol which is characteristic ones of glycopeptide having the formula (II). The Rf values of the product measured in accordance with Example 1 were 0.44 and 0.48 which are corresponded to those of the known bleomycin A$_2$.

The activity to Mycobacterium Smegmatis 607 was 925 U/mg.

EXAMPLE 7

100 mg. (0.064 m mol) of powdery 3-morpholino propylaminophleomycin (Cu-containing hydrochloride) which has the absorption maximum of $E_{1cm}^{1\%}$ 150 at 244 m$\mu$, and the other absorption maximum of $E_{1cm}^{1\%}$ 54 at 300 m$\mu$, and end absorption of ultraviolet absorption spectrum in methanol (activity to Mycrobacterium Smegmatis 607 of 474 U/mg) was dissolved in 5 m of water and 0.1 N NaOH was added to adjust to pH 7.5 and 50 mg 0.575 m mol of manganese dioxide was suspended and reacted at a room temperature for 58 hours with stirring. After the reaction, the solution was filtered. The filtrate was absorbed and eluted by using a chromatography.

The unreacted phleomycin was eluted in the fraction of 0.29 M of sodium chloride elute and the object product of 3-morpholino propylamino-bleomycin (Cu-containing hydrochloride) was eluted in the fraction of 0.34 M of sodium chloride elute. The solution of 3-morpholinopropylamino-bleomycin (Cu-containing hydrochloride) eluted as the latter fraction was treated in accordance with Example 1 to obtain 50 mg of blue powdery 3-morpholino propylamino-bleomycin. The product has the absorption maximum of $E_{1cm}^{1\%}$ 159 at 244 m$\mu$, and the absorption maximum of $E_{1cm}^{1\%}$ 128 at 293 m$\mu$ and end absorption of ultraviolet absorption spectrum in methanol which is characteristic ones of glycopeptide having the formula (II). The Rf values of the product measured in accordance with Example 1 were 0.74 and 0.58 which are corresponded to those of the known 3-morpholino propylaminobleomycin (Cu-containing hydrochloride). The activity of Mycrobacterium Smegmatis 607 and 587 U/mg.

EXAMPLE 8

100 mg (0.066 m mol) of powdery 3-N, N-dimethylaminopropylamino-phleomycin (Cu-containing hydrochloride) which has the absorption maximum of $E_{1cm}^{1\%}$ 149 at 244 m$\mu$ and the other absorption maximum of $E_{1cm}^{1\%}$ 53 at 300 m$\mu$ and end absorption of ultraviolet absorption spectrum in methanol. (activity to Mycrobacterium Smegmatis 607 of 648 U/mg) was dissolved in 5 ml of water and 50 mg and 0.1 N-NaOH was added to adjust to pH 9.0 of manganese dioxide was suspended in the solution and reacted at a room temperature for 48 hours with stirring.

After the reaction, the solution was filtered. The filtrate was absorbed and eluted by using a chromatography. The unreacted phleomycin was eluted in the fraction of 0.28 M of sodium chloride elute and the object product of 3-N, N-dimethylaminopropylaminobleomycin (Cu-containing hydrochloride) was eluted in 0.33 M of sodium chloride elute.

The solution of the product eluted as the latter fraction was treated in accordance with Example 1 to obtain 65 mg of blue powdery 3-N, N-dimethylaminopropylamino-bleomycin (Cu-containing, hydrochloride). The product has the absorption maximum of $E_{1cm}^{1\%}$ 162 at 244 m$\mu$ and the absorption maximum of $E_{1cm}^{1\%}$ 134 at 293 m$\mu$, and end absorption of ultraviolet absorption spectrum in methanol which is characteristic ones of glycopeptide having the formula (II). The Rf value of the product measured in accordance with Example 1 were 0.44 and 0.55 which are corresponded to those of the known 3-N, N-dimethylaminopropylamino-bleomycin. The activity to Mycrobacterium Smegmatis 607 and 820 U/mg.

Having now fully described the invention, it will be apparent to one of ordinary skill in the art that many changes and modifications can be made thereto without departing from the spirit or scope of the invention as set forth herein.

What is claimed and intended to be covered by Letters Patent is:

1. A process for preparing stable bleomycin group antibiotics having the partial structure

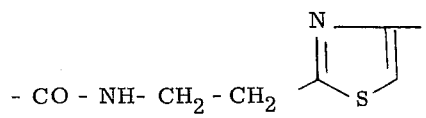

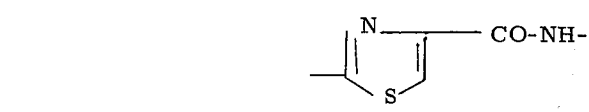

which comprises oxidizing the corresponding phleomycin group antibiotic having the partial structure

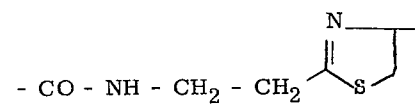

with potassium ferricyanide or manganese dioxide at 0° to 50°C, for 20–240 hours at pH 6.5 – 9, employing 1 –50 moles of oxidizing agent per mole of phleomycin group antibiotic, said phleomycin group antibiotic being selected from the group consisting of phleomycin D$_1$, E, G, a mixture thereof, 3-S, S-dimethylmercaptopropylamino-phleomycin, 3-morpholinopropylaminophleomycin, 3-N, N-dimethylaminopropylaminophleomycin and YA-56 and separating the stable bleomycin group antibiotic.

* * * * *